(12) United States Patent
Marteney et al.

(10) Patent No.: US 9,138,300 B2
(45) Date of Patent: Sep. 22, 2015

(54) DENTAL SEPARATOR APPARATUS

(71) Applicant: Bowater, LLC, Ash Fork, AZ (US)

(72) Inventors: Steve Marty Marteney, San Dimas, CA (US); John Hamilton, Santa Clarita, CA (US)

(73) Assignee: Bowater, LLC, Ash Fork, AZ (US)

( * ) Notice: Subject to any disclaimer, the term of this patent is extended or adjusted under 35 U.S.C. 154(b) by 0 days.

(21) Appl. No.: 14/146,925

(22) Filed: Jan. 3, 2014

(65) Prior Publication Data

US 2014/0120497 A1 May 1, 2014

Related U.S. Application Data

(62) Division of application No. 13/174,099, filed on Jun. 30, 2011, now Pat. No. 8,647,120.

(51) Int. Cl.
*A61C 7/00* (2006.01)
*A61C 5/12* (2006.01)
*A61C 3/00* (2006.01)

(52) U.S. Cl.
CPC .. *A61C 5/127* (2013.01); *A61C 3/00* (2013.01)

(58) Field of Classification Search
CPC ............ A61C 5/127; A61C 3/14; A61C 3/16; A61C 3/162; A61C 7/10; A61C 3/164; A61C 7/125; B25B 7/12; B25B 7/10; B25B 1/123; B25B 7/00
USPC ............. 433/136–138, 39, 80, 153–155, 157, 433/159; 81/57.17, 342–348, 385, 484
See application file for complete search history.

(56) References Cited

U.S. PATENT DOCUMENTS

| | | | |
|---|---|---|---|
| 368,988 A | 8/1887 | Williams | |
| 421,952 A | 2/1890 | Marshall | |
| 424,790 A * | 4/1890 | Ivory | 433/158 |
| 425,067 A | 4/1890 | Farrar | |
| 427,338 A | 5/1890 | Marshall | |
| 440,509 A | 11/1890 | Sawhill | |
| 465,555 A | 12/1891 | Cross et al. | |
| 486,112 A | 11/1892 | Kuns | |
| 511,619 A | 12/1893 | Ivory | |
| 545,754 A | 9/1895 | Wishart | |
| 600,257 A * | 3/1898 | Capwell | 433/149 |
| 819,136 A | 5/1906 | Herman | |
| 847,778 A | 3/1907 | Ivory | |
| 1,306,696 A | 6/1919 | Ivory | |

(Continued)

OTHER PUBLICATIONS

Non-Final Office Action mailed Nov. 26, 2012, U.S. Appl. No. 13/174,099.

(Continued)

*Primary Examiner* — Heidi M Eide
(74) *Attorney, Agent, or Firm* — Berkeley Law & Technology Group, LLP

(57) ABSTRACT

A tooth separator apparatus, according to one embodiment, includes a tong having two resilient arms that are biased in an open position and having a wedge at each end of each arm. A drive shaft moves a compression member to overcome the resiliency of the arms and move them and the wedges in a closing direction for separating the teeth. The drive shaft can also move the compression member in the opposite direction to release the closing force on the arms and thereby permit their resiliency to allow them and the wedges to move to an open position.

16 Claims, 3 Drawing Sheets

(56) References Cited

U.S. PATENT DOCUMENTS

| | | | |
|---|---|---|---|
| 1,456,294 A | 5/1923 | Arrowsmith | |
| 1,464,532 A | 8/1923 | Ivory | |
| 1,829,898 A | 11/1931 | Ivory | |
| 1,908,145 A * | 5/1933 | Harper | 433/158 |
| 2,311,141 A | 2/1943 | True | |
| 2,629,930 A | 3/1953 | Lane | |
| 2,647,315 A | 8/1953 | Dvorak | |
| 3,913,228 A | 10/1975 | Wallshein | |
| 4,718,852 A | 1/1988 | Galler | |
| 5,993,210 A * | 11/1999 | Godfrey | 433/159 |
| 6,206,697 B1 | 3/2001 | Hugo | |
| 6,325,625 B1 | 12/2001 | Meyer | |
| 6,666,683 B2 | 12/2003 | Mungcal | |
| 7,165,970 B2 | 1/2007 | Anderson | |
| D589,615 S | 3/2009 | Doenges et al. | |
| 7,722,353 B2 | 5/2010 | Graham | |
| 2002/0155410 A1 | 10/2002 | Bills | |
| 2007/0172793 A1 | 7/2007 | Doenges et al. | |
| 2008/0064009 A1 | 3/2008 | Clark | |
| 2008/0113315 A1 | 5/2008 | Beggs | |
| 2009/0258325 A1 | 10/2009 | Zand | |
| 2009/0286200 A1 | 11/2009 | Ho | |
| 2013/0004914 A1 | 1/2013 | Marteney et al. | |

OTHER PUBLICATIONS

Final Office Action mailed Mar. 12, 2013, U.S. Appl. No. 13/174,099.
Examiner Interview Summary mailed Jun. 4, 2013, U.S. Appl. No. 13/174,099.
Non-Final Office Action mailed Aug. 21, 2013, U.S. Appl. No. 13/174,099.
Examiner Interview Summary mailed Sep. 13, 2013, U.S. Appl. No. 13/174,099.
Notice of Allowance mailed Oct. 3, 2013, U.S. Appl. No. 13/174,099.

* cited by examiner

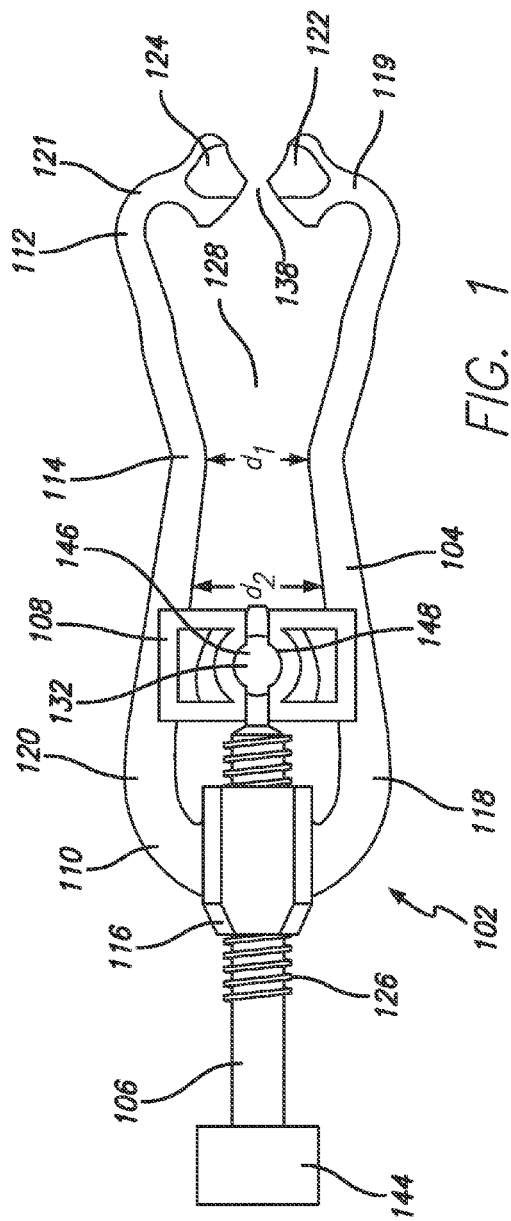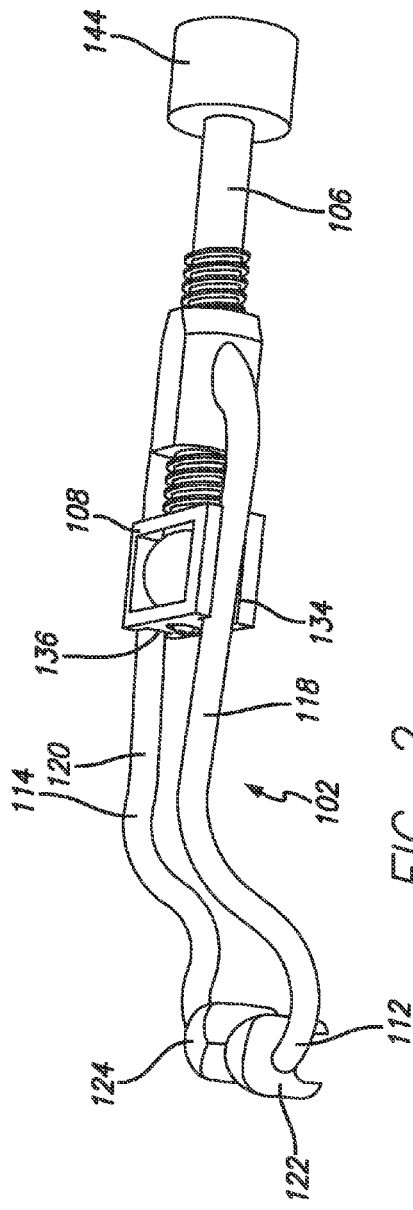

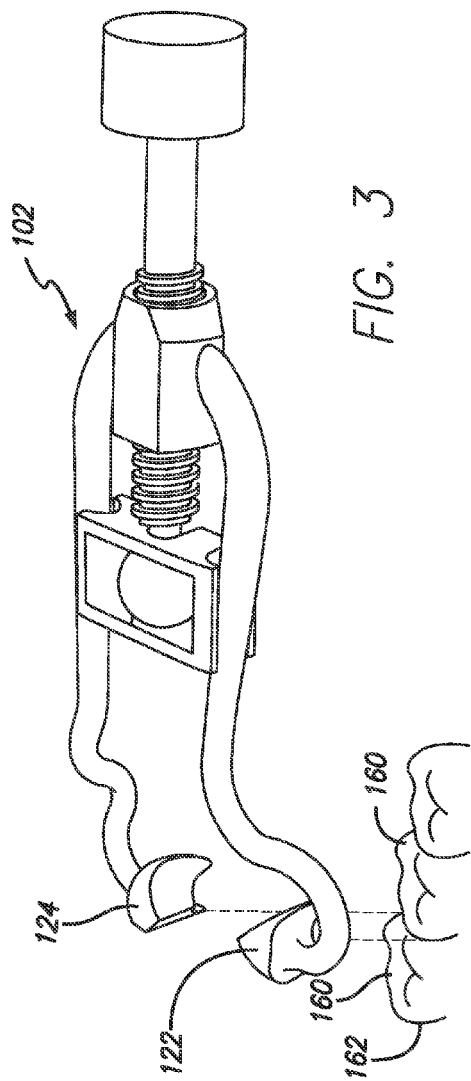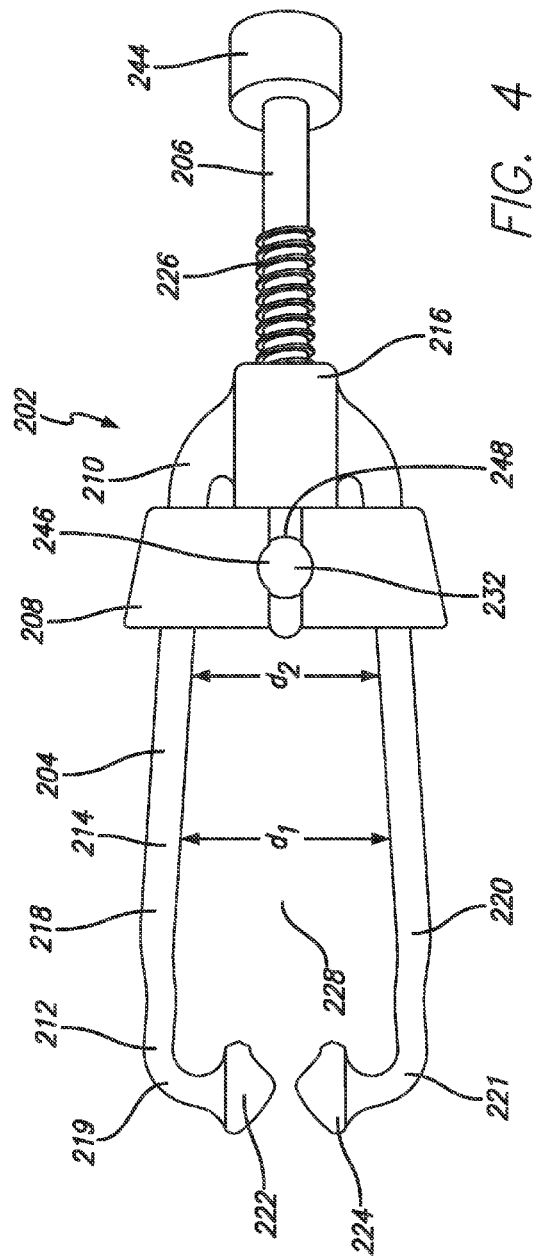

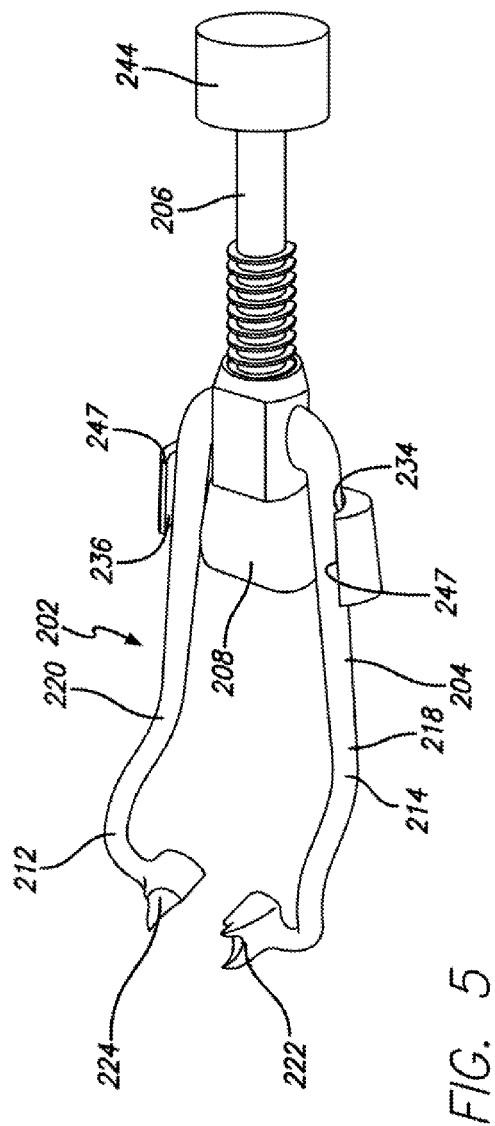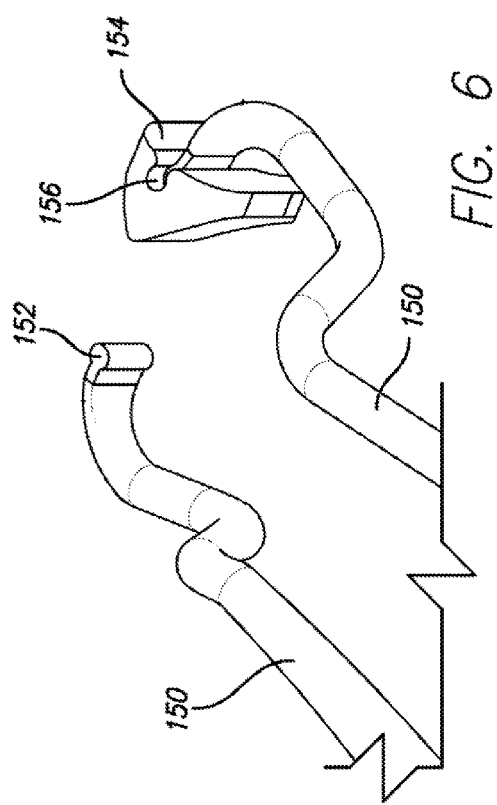

DENTAL SEPARATOR APPARATUS

CROSS REFERENCE TO RELATED APPLICATION

This application is a divisional of, and claims the benefit of priority from U.S. application Ser. No. 13/174,099, entitled "Dental Separator Apparatus and Method", filed on Jun. 30, 2011, which such application is incorporated herein by reference in its entirety.

1. Field of Invention

This relates to dental devices and methods. More specifically this relates to devices and methods for temporarily separating adjacent teeth in order to permit various dental procedures on one or both of these teeth.

2. Background

One challenge facing dentists while treating patients is that presented by cavities that are found at an interproximal location. In order to remove the decayed portion of a tooth with a drill and to fill the tooth with a filler material, it often is necessary to temporarily separate the adjacent teeth in order to provide adequate space to allow for shrinkage of the filler material and to maintain a tight contact between the adjacent teeth.

Small wooden wedges often are used in conjunction with a matrix foil of some type to seal the gingival portion of the preparation. The matrix foil is used to restore the contour of the tooth to that which existed prior to the decay. Known devices which separate adjacent teeth apply pressure to the matrix foil between the adjacent teeth and hold the wooden wedge in place to seal the gingival margin of the preparation. This allows for temporarily separating or creating a greater space between the adjacent teeth which in turn allows for placement of the filler material. When the separators are removed the teeth return to their previous position. However because of the space created by the separators and the filler material that is placed on the tooth, a tight contact between the adjacent teeth should exist after the dental procedure is completed even if there previously had not been tight contact prior to the commencement of the procedure.

Known devices for temporarily separating adjacent teeth include dental rings. A dental ring is a metal device having a generally circular, open-ended shape with a flange at each end of the ring. A pair of manual forceps is used to grasp the ring and force it open thus spreading apart the flanges. The ring is then positioned around one of the two adjacent teeth with the forceps, and when the forceps are released, the flanges act to separate the teeth. However dental rings have disadvantages in that they and the forceps can be clumsy to work with, and a dentist's vision sometimes can be blocked when placing a ring around a tooth in certain locations in a patient's mouth. Also it sometimes happens that while being inserted into a patient's mouth, the forceps lose their grip on the rings which results in the rings snapping away from the forceps and lodging at unintended locations in the mouth. Also certain types of rings cannot be used with certain matrices, such as the Tofflemire matrix system, due to the interference of these rings with these matrices.

SUMMARY OF THE ILLUSTRATED EMBODIMENTS

Broadly speaking, certain embodiments of the invention relate to a tooth separator apparatus that includes a pair of tongs having two arms constructed of a resilient material and having a wedge disposed at the end of each arm. An expander member is coupled to the two arms, and a drive shaft is coupled to the expander member. When a user, such as a dentist, moves or rotates the drive shaft, the expander member is moved into a position which causes the two arms and wedges to separate from one another by a distance sufficient to permit the arms and wedges to be inserted in a patient's mouth and positioned adjacent to interdental surfaces of two teeth that are to be separated. When the user rotates the drive shaft in the reverse direction, the expander member returns to its original position thereby releasing the separating force on the resilient arms and permitting them and the wedges to move in a closing direction with sufficient force to separate the adjacent teeth.

In an alternative embodiment, the resilient arms are biased in an open position. A drive shaft moves a compression member to overcome the resiliency of the arms and move them and the wedges in a closing direction for separating the teeth. The drive shaft can also move the compression member in the opposite direction to release the closing force on the arms and thereby permit their resiliency to allow them and the wedges to move to an open position.

According to one embodiment an apparatus comprises a pair of tongs having a proximate end and a distal end, and having a first arm connected to a second arm at the proximate end of the tongs. The first arm has a first arm end and the second arm has a second arm end, both of which are disposed at the distal end of the tongs. An actuator is attached to the tongs and operable to exert a spreading force on the first and second arms. The actuator is configured to maintain the spreading force on the first and second arms when the user is not grasping the actuator, and is further operable to release the spreading force from the first and second arms. The first and second arms are configured so that when the separating force is exerted by the actuator, the first and second arms are separated by a distance sufficient to allow for insertion of the first and second arm ends into the mouth and for placement of the first and second arm ends between the adjacent teeth. The first and second arms are constructed of a resilient material and are formed to bias the first and second arm ends toward each other with sufficient closing force to separate the adjacent teeth when the actuator releases the separating force from the first and second arms.

In another aspect, the actuator is a drive shaft coupled to the first and second arms and configured for movement between a first position and a second position. The drive shaft is further configured to exert the separating force on the first and second arms when the drive shaft is in the first position and to remove the separating force from the first and second arms when the drive shaft is moved from the first position to the second position.

In yet another aspect, the actuator includes an expander member coupled to the first and second arms. The expander member is disposed between the first and second arms and configured to exert the separating force on the first and second arms.

In yet another aspect, the first and second arms are shaped such that when the separating force is not exerted on them, the first and second arms are separated by a first distance at a first location of the tongs and by a second distance at a second location of the tongs, wherein the first distance is less than the second distance. The expander member is disposed adjacent to the first location of the tongs when the spreading force is exerted by the expander member and disposed adjacent to the second location of the tongs when the spreading force is not exerted by the expander member.

In yet another embodiment, an apparatus comprises a pair of tongs having a proximate end and a distal end, and further having a first arm connected to a second arm at the tongs' proximate end. The first arm has a first arm end and the second arm has a second arm end, both of which are disposed at the distal end of the tongs. The apparatus further includes means for exerting a spreading force on the first and second arms and means for maintaining the spreading force on the first and second arms when the user is not grasping the tongs, and for releasing the spreading force from the first and second arms. The first and second arms are configured so that when the separating force is exerted, the first and second arms are separated by a distance sufficient to allow for insertion of the first and second arm ends into a mouth of a patient and for placement of the first and second arm ends between adjacent teeth in the patient's mouth. The first and second arms are formed to bias the first and second arm ends toward each other with sufficient closing force to separate the adjacent teeth when the separating force is released from the first and second arms.

In yet another alternative embodiment, a method of forcing apart adjacent teeth of a dental arch of a mouth includes inserting at least a portion of a pair of tongs into the mouth. The tongs have a proximate end and a distal end, and further have a first arm connected to a second arm at the proximate end. The first and second arms are constructed of a resilient material for biasing the first and second arms in a closing direction. The first arm has a first arm end and the second arm has a second arm end, both of which are disposed at the distal end of the tongs. The first and second arm ends are positioned adjacent to interdental surfaces of the adjacent teeth. A drive shaft, which is coupled to the first and second arms, is moved from a first position to a second position thereby removing a separating force from the resilient first and second arms and thereby allowing the first and second arm ends to move toward each other with sufficient closing force to separate the adjacent teeth.

In one aspect, the drive shaft is moved from the second position to the first position thereby exerting the separating force on the first and second arms and moving the first and second arm ends apart from each other. These ends are moved apart by a distance sufficient to allow for removal of the first and second arm ends from a position that is adjacent to interdental surfaces of the adjacent teeth and to allow for removal of the at least the portion of the tongs from the mouth.

In another aspect, the moving of the drive shaft from the first position to the second position moves an expander member that is coupled to the drive shaft and slidably engaged with the first and second arms. The expander member is disposed between the first and second arms and configured to exert the separating force when the drive shaft is in the first position and to release the separating force when the drive shaft is moved from the first position to the second position.

In yet another embodiment, the apparatus comprises a pair of tongs and a drive shaft. The tongs have a proximate end and a distal end and further have a first arm connected to a second arm at the proximate end. The first arm has a first arm end and the second arm has a second arm end, both of which are disposed at the distal end of the tongs. The drive shaft is coupled to the first and second arms and configured for movement between a first position and a second position. The drive shaft is further configured to exert a closing force on the first and second arms when the drive shaft is moved from the second position to the first position thereby moving the first and second arm ends toward each other with sufficient closing force to separate the adjacent teeth. The drive shaft is further configured remove the closing force from the first and second arms when the drive shaft is moved from the first position to the second position. The first and second arms are constructed of a resilient material for biasing the first and second arm ends away from each other when the closing force is removed from them, thereby separating the first and second arm ends by a distance sufficient to allow for insertion of the first and second arm ends into the mouth and for placement of the first and second arm ends between the adjacent teeth.

In another aspect, the drive shaft is coupled to the first and second arms with a compression member that is configured for slidable engagement with the first and second arms. The compression member is disposed between the first and second arms and configured to exert the closing force when the drive shaft is in the first position and to release the closing force when the drive shaft is moved from the first position to the second position.

In yet another aspect, the first and second arms are shaped such that when the closing force is not exerted on the first and second arms, they are separated by a first distance at a first location of the tongs and by a second distance at a second location of the tongs, wherein the first distance is greater than the second distance. The compression member is disposed adjacent to the first location of the tongs when the drive shaft is in the first position and disposed adjacent to the second location of the tongs when the drive shaft is in the second position.

In yet another aspect, the tongs have a center portion disposed between the tongs proximate end and the tongs distal end. The first and second arms are shaped such that when the closing force is not exerted on them, they are separated by a first distance at the center portion of the tongs and by a second distance at the proximate end of the tongs, wherein the first distance is greater than the second distance. The compression member is disposed adjacent to the proximate end of the tongs when the drive shaft is in the second position and disposed adjacent to the center portion of the tongs when the drive shaft is in the first position.

In yet another embodiment, the apparatus comprises a pair of tongs having a proximate end and a distal end, and further having a first arm connected to a second arm at the proximate end of the tongs. The first and second arms are constructed of a resilient material for biasing the first and second arms in an opening direction. The first arm has a first arm end and the second arm has a second arm end, both of which are disposed at the distal end of the tongs. The apparatus further includes means for exerting a closing force on the first and second arms, for maintaining the closing force on the first and second arms when the user is not grasping the tongs, and for releasing the closing force from the first and second arms. The first and second arms are configured so that when the closing force is released, they are separated by a distance sufficient to allow for insertion of the first and second arm ends into the mouth and for placement of the first and second arm ends between the adjacent teeth.

In yet another embodiment, at least a portion of a pair of tongs is inserted into a mouth of a patient. The tongs have a proximate end and a distal end and are comprised of a first arm connected to a second arm at the proximate end. The first arm has a first arm end and the second arm has a second arm end, both of which are disposed at the distal end of the tongs. The first and second arms are constructed of a resilient material for biasing the first and second arms in an opening direction. The first and second arm ends are positioned adjacent to interdental surfaces of the adjacent teeth. A drive shaft is moved from a second position to a first position thereby providing a closing force on the first and second arms and moving the first and second arm ends toward each other with sufficient force to separate the adjacent teeth. The drive shaft is coupled to the first and second arms and configured for movement between the first position and the second position.

In another aspect, the drive shaft is moved from the first position to the second position thereby removing the closing force on the first and second arms and thereby allowing the first and second arm ends to move apart from each other by a distance sufficient to allow for their removal from the position that is adjacent to the interdental surfaces of the adjacent teeth and to allow for removal of the at least the portion of the tongs from the mouth.

In another aspect, the moving of the drive shaft from the second position to the first position includes moving a compression member coupled to the drive shaft and slidably engaged with the first and second arms. The compression member is disposed between the first and second arms and configured to exert the closing force when the drive shaft is in the first position and to remove the closing force when the drive shaft is moved from the first position to the second position.

There are additional aspects to the present inventions. It should therefore be understood that the preceding is merely a brief summary of some embodiments and aspects of the present inventions. Additional embodiments and aspects are referenced below. It should further be understood that numerous changes to the disclosed embodiments can be made without departing from the spirit or scope of the inventions. The preceding summary therefore is not meant to limit the scope of the inventions. Rather, the scope of the inventions is to be determined by appended claims and their equivalents.

BRIEF DESCRIPTION OF THE DRAWINGS

These and/or other aspects and advantages of the present invention will become apparent and more readily appreciated from the following description of certain embodiments, taken in conjunction with the accompanying drawings of which:

FIG. 1 is a bottom plan view of a tooth separator apparatus in accordance with one embodiment of the invention;

FIG. 2 is a top perspective view of the tooth separator apparatus of FIG. 1;

FIG. 3 is a perspective view of the tooth separator apparatus of FIG. 1 showing its position above adjacent teeth that are to be restored;

FIG. 4 is a top plan view of a tooth separator apparatus in accordance with another embodiment of the invention;

FIG. 5 is a bottom perspective view of the tooth separator apparatus of FIG. 4; and FIG. 6 is a top perspective view of the arms and a removable wedge of a tooth separator apparatus in accordance with another embodiment of the invention.

DETAILED DESCRIPTION

The following description is of the best mode presently contemplated for carrying out the invention. Reference will be made in detail to embodiments of the present invention, examples of which are illustrated in the accompanying drawings, wherein like reference numerals refer to like elements throughout. It is understood that other embodiments may be used and structural and operational changes may be made without departing from the scope of the present invention.

FIGS. 1, 2 and 3 show a separator apparatus 102 for use in temporarily forcing apart adjacent teeth 160 in a dental arch 162 of a mouth according to an embodiment of the invention. This can be used along with a wood wedge (not shown) so that the separator apparatus 102 separates the adjacent teeth 160 to allow for the shrinkage of the composite material between the teeth 160 and so that the wood wedge can hold a matrix foil in position. Alternatively the separator apparatus 102 can be used without a wood wedge so that the separator apparatus 102 itself maintains the tooth separation while a user, such as a dentist, performs dental restorative work. The separator apparatus 102 is comprised of a pair of tongs 104, an expander member 108, and a drive shaft 106 having a knob 144. In the illustrated embodiment the tongs 104 are about 1.875 inches in length, and the drive shaft 106 is about 1.75 inches in length. The face profile of the illustrated expander member 108 is about 0.25 inches in width (extending longitudinally with respect to the separator apparatus 102) and about 0.5 inches in length (extending transversely with respect to the separator apparatus 102) as seen in the plan view of FIG. 1. However alternative embodiments of the invention can include components having other dimensions without departing from the spirit of the inventions.

The tongs 104 have a proximate end 110, a distal end 112 and a center portion 114 disposed between the proximate and distal ends 110, 112. The tongs 104 further have a housing 116 that is disposed at the proximate end 110 and that defines a longitudinally-oriented port having internal threads. The tongs 104 also have a first arm 118 connected to a second arm 120 at the proximate end 110 of the tongs 104. The first arm 118 has a first arm end 119, and the second arm 120 has a second arm end 121, both of which are disposed at the distal end 112 of the tongs 104. A first wedge 122 is connected to the first arm end 119 and a second wedge 124 is connected to the second arm end 121. Each of the first and second wedges 122, 124 has a shape that is configured to engage interdental surfaces of the adjacent teeth 160. Wedges, such as the first and second wedges 122, 124, are sometimes referred to as end point tools, interchangeable end points, embrasure holding pins, separating embrasure ends, accessory attachments, hard points, attached points, and tool points.

As viewed from the bottom as in FIG. 1, the first and second arms 118, 120 are curve-shaped such that they curve inward as they extend from the proximate end 110 of the tongs 104 to the tongs center portion 114 and then flare outward as they continue in extension from the tongs center portion 114 toward the tongs distal end 112 at which location they curve inward so that the first and second wedges 122, 124 point toward each other. Thus when the expander member 108 is positioned near the proximate end 110 of the tongs 104 as shown in FIG. 1, the arms are separated by a first distance $d_1$ at the center portion 114 of the tongs 104 and by a second distance $d_2$ that is greater than the first distance $d_1$ and that is at a location that is closer to the proximate end 110 of the tongs 104. The first and second arms 118, 120 are constructed of a resilient material such as, for example, stainless steel, nitinol or titanium, and alternatively can be constructed of other resilient materials, as well.

As best seen in FIG. 2, the knob 144 of the drive shaft 106 and the first and second wedges 122, 124 provide three imaginary points defining an imaginary plane (not shown in FIG. 2) above which the entire separator apparatus 102 extends. Thus the first and second arms 118, 120 are shaped so that they curve in a downward direction as they extend from the center portion 114 of the tongs 104 toward the tongs distal end 112. This downward curve facilitates the placement of the first and second arms 118, 120 over a lip of a patient's mouth so that the first and second wedges 122, 124 can be more easily oriented between adjacent teeth.

The expander member 108 is comprised of a rigid piece having a generally rectilinear-shaped profile when viewed from a top or bottom plan view of the separator apparatus 102. The expander member 108 defines a first groove 134 configured to slidably mate with the first arm 118 of the tongs 104 and a second groove 136 configured to slidably mate with the second arm 120.

The drive shaft 106 has external axial threads 126 configured to rotatably engage the internal threads of the housing 116 of the tongs 104. Thus the drive shaft 106 is configured for a generally linear, generally longitudinal movement between a first position and a second position in response to a rotation of the drive shaft 106 within the tongs housing 116. In the illustrated embodiment the second position is the position of the drive shaft 106 as it is shown in FIGS. 1 and 2, i.e., where the drive shaft 106 is positioned as far as possible away from the tongs distal end 112. The first position, on the other hand, is a position where the drive shaft 106 has advanced in a direction toward the tongs distal end 112 to a point where the expander member 108 is disposed adjacent to the tongs center portion 114 and where a distal end of the drive shaft 106 (i.e., the end furthest from the knob 144) would be located at about the position shown at reference numeral 128 of FIG. 1.

The expander member 108 is coupled to the drive shaft 106 by a ball joint 132 so that the expander member 108 moves in a generally linear, generally longitudinal direction in response to the movement of the drive shaft 106. In the illustrated embodiment, the ball joint 132 is comprised of a spherical portion 146 formed adjacent to the distal end of the drive shaft 106 and a cavity 148 defined by the expander member 108. The spherical portion 146 is configured to seat within the cavity 148 so that the spherical portion 146 can freely rotate within the cavity 148. While the spherical portion 146 and the cavity 148 are exposed to view in the illustrated embodiment, alternative embodiments include a cover (not shown) attached to the expander member 108 so that the spherical portion 146 and the cavity 148 are enclosed by the cover and are not exposed to view.

When the drive shaft 106 is moved from the second position to the first position, the expander member 108 slides from a position that is adjacent to the proximate end 110 of the tongs 104 (as illustrated in FIGS. 1 and 2) to a position adjacent to the center portion 114 of the tongs 104. Because the center portion 114 of the tongs 104 is the location where the first and second arms 118, 120 are separated by the relatively short first distance $d_1$ that is less than the second distance $d_2$, this movement of the expander member 108 presses outward against the resilient first and second arms 118, 120 and exerts a separating force on them, thereby causing the arms as well as the first and second wedges 122, 124 to move apart. When the expander member 108 is positioned adjacent to the tongs center portion 114, the arms and wedges are separated by a distance sufficient to allow for their insertion into the patient's mouth and for placement of the wedges 122, 124 between the adjacent teeth 160 as illustrated by the broken lines of FIG. 3. On the other hand when the drive shaft 106 is rotated in the reverse direction so that it is moved from the first position to the second position, the expander member 108 slides in the reverse direction toward the proximate end 110 of the tongs 104. This thereby removes the separating force from the first and second arms 118, 120, and allows them and the wedges to move in a closing direction due to the resiliency of the first and second arms 118, 120. Thus the drive shaft 106 and the expander member 108 comprise means for exerting a spreading force on the first and second arms 118, 120, for maintaining this spreading force when the user is not grasping the tongs 104 or any other component of the separator apparatus 102, and for releasing the spreading force.

The first and second arms 118, 120 are formed to bias the first and second wedges 122, 124 toward each other with sufficient closing force to separate the adjacent teeth when the separating force is removed. However when the separating force is removed, a gap 138 remains between the first and second wedges 122, 124, and their closing force is limited to no more than a predetermined amount in order to reduce the chance of damaging the teeth which might otherwise happen if the closing force is excessive. In the illustrated embodiment the first and second arms 118, 120 are configured to provide a closing force of twenty (20) pounds at a four (4) millimeter separation. However alternative embodiments may incorporate closing forces of different magnitudes without departing from the spirit of the inventions. The illustrated embodiment is advantageous in that regardless of how much manual twisting is exerted on the drive shaft 106, the separator apparatus 102 will only exert the maximum predetermined separation force on the adjacent teeth 160 thus reducing the chance of damaging them. This embodiment is also advantageous in that once the first and second arms 118, 120 are separated, the spreading force can be maintained on the arms when the user is not grasping the tongs 104 or any other part of the separator apparatus 102, thus providing ease of use.

In the illustrated embodiment, the tongs 104, the housing 116, the first and second arms 118, 120, and the first and second wedges 122, 124 are constructed of metal and are monolithically formed. However in alternative embodiments, the wedges are removably attached to the arms. FIG. 6 illustrates an alternative embodiment whereby each of two arms 150 of a pair of tongs terminates in a post 152 that is monolithically formed with each arm 150. A wedge 154 defines a groove 156 that can mate with the post 152 so that the wedge 154 can slide onto the post 152 in a direction that is generally transverse to a direction of movement of the posts 152 as the arms 150 move in an open or closed direction. Thus by being configured to slidably engage the arms 150, a plurality of different wedges or other tools having different profiles, shapes or functions can easily be used with a single separator apparatus thereby permitting its use for different dental procedures or for a wide variety of tooth profiles. While FIG. 6 illustrates one means for removably attaching wedges to arms, other means for accomplishing this includes accessory sockets, tool bits in chucks, tool templates, friction fittings, and precision attachments.

Referring again to FIGS. 1 and 2, in operation a user grasps the knob 144 with his/her fingers and rotates it and the drive shaft 106 so that the expander member 108 slides from the location adjacent to the proximate end 110 of the tongs 104 to the location adjacent to the tongs center portion 114. As the expander member 108 moves, it exerts a spreading force on the resilient first and second arms 118, 120 thereby expanding or spreading them and the first and second wedges 122, 124 apart. Once the expander member 108 is positioned adjacent to the tongs center portion 114 and the first and second wedges 122, 124 are spread apart, the user no longer needs to grasp the knob 144 or any other portion of the drive shaft 106 or the tongs 104 in order to maintain the separation of the first and second wedges 122, 124.

Next the user inserts the wedges 122, 124 and a portion of the first and second arms 118, 120 into the mouth of a patient, and then positions the wedges 122, 124 adjacent to interdental surfaces of the adjacent teeth that are to be separated. The user then grasps the knob 144 and rotates the drive shaft 106 in the opposite direction, thereby sliding the expander member 108 back to its starting position adjacent to the tongs proximate end 110. As the expander member 108 moves to this position, the separating force is removed from the first and second arms 118, 120. The resiliency of the first and second arms 118, 120 causes them and the first and second wedges 122, 124 to move toward each other in a closing direction thereby exerting a closing force on these wedges that is sufficient to separate the adjacent teeth. After the dental work is completed on one or both of the adjacent, separated teeth, the user again rotates the knob 144 and the drive shaft 106 so that the expander member 108 slides to the position that is adjacent to the tongs center portion 114. This causes the first and second wedges 122, 124 to again separate from one another so that they can be removed from contact with the adjacent teeth and can be easily removed from the patient's mouth.

While the drive shaft 106 and the expander member 108 of FIGS. 1-3 constitute one type of actuator that is operable to exert the spreading force on the tongs 104, alternative embodiments include other types of actuators for spreading the arms of tongs and for maintaining this spreading force when users are not grasping these actuators.

The embodiment of FIGS. 1-3 generally involves a separator apparatus having resilient arms that are biased in a closed direction so that an actuator can move and overcome the resiliency of the arms in order to spread them apart. Alternative embodiments, on the other hand, include a separator apparatus having resilient arms that are biased in an opened direction so that an actuator can move and overcome their resiliency in order to force the arms in a closing direction. FIGS. 4 and 5 show such a separator apparatus 202 for use in temporarily separating adjacent teeth according to another embodiment of the invention. The separator apparatus 202 is comprised of a pair of tongs 204, a compression member 208, and a drive shaft 206 having a knob 244. These components of the separator apparatus 202 have approximately the same overall dimensions and are constructed of the same materials as the corresponding components described above for the embodiment of FIGS. 1-3. Referring still to FIGS. 4-5, the tongs 204 have a proximate end 210, a distal end 212 and a center portion 214 disposed between the proximate and distal ends 210, 212. The tongs 204 further have a housing 216 that is disposed at the proximate end 210 and that defines a longitudinally-oriented port having internal threads. The tongs 204 also have a first arm 218 connected to a second arm 220 at the proximate end 210 of the tongs 204. The first arm 218 has a first arm end 219, and the second arm 220 has a second arm end 221, both of which are disposed at the distal end 212 of the tongs 204. A first wedge 222 is connected to the first arm end 219, and a second wedge 224 is connected to the second arm end 221. Each of the first and second wedges 222, 224 has a shape that is configured to engage interdental surfaces of the adjacent teeth and are generally the same as the wedges described above in connection with FIGS. 1-3.

As viewed from the top as in FIG. 4, the first and second arms 218, 220 are shaped such that they are separated by a progressively increasing distance as they extend from the proximate end 210 of the tongs 204 to the tongs center portion 214 and from the center portion 214 toward the tongs distal end 212 at which location the first and second arms 218, 220 curve inward so that the first and second wedges 222, 224 point toward each other. Thus when the compression member 208 is positioned near the proximate end 210 of the tongs 204 as shown in FIG. 4, the arms are separated by a first distance $d_1$ at the center portion 214 of the tongs 204 and by a second distance $d_2$ that is less than the first distance $d_1$ and that is at a location that is closer to the proximate end 210 of the tongs 204.

As best seen in FIG. 5, the knob 244 of the drive shaft 206 and the first and second wedges 222, 224 provide three imaginary points defining an imaginary plane (not shown) below which the entire separator apparatus 202 extends when viewed from the bottom. Thus as viewed from the bottom the first and second arms 218, 220 are shaped so that they curve in an upward direction as they extend from the center portion 214 of the tongs 204 in a direction toward the tongs distal end 212. This upward curve facilitates the placement of the first and second arms 218, 220 over a lip of a patient's mouth (when the separator apparatus 202 is oriented as shown in FIG. 4) so that the first and second wedges 222, 224 can be more easily oriented between adjacent teeth.

The compression member 208 is comprised of a rigid piece having a generally rectilinear-shaped profile when viewed from a top or bottom plan view of the separator apparatus 202. The compression member 208 defines a first channel 234 configured to slidably mate with the first arm 218 of the tongs 204 and a second channel 236 configured to slidably mate with the second arm 220. Each of the first and second channels 234, 236 is formed in part by an outer wall 247, or flange, that extends around an outside portion of each of the first and second arms 218, 220 as best seen in FIG. 5.

The drive shaft 206 has external axial threads 226 configured to rotatably engage the internal threads of the housing 216 of the tongs 204. Thus the drive shaft 206 is configured for a generally linear, generally longitudinal movement between a first position and a second position in response to a rotation of the drive shaft 206 within the tongs housing 216. In the illustrated embodiment the second position is the position of the drive shaft 206 as it is shown in FIGS. 4 and 5, i.e., where the drive shaft 206 is positioned as far as possible away from the tongs distal end 212. The first position, on the other hand, is a position where the drive shaft 206 has advanced in a direction toward the tongs distal end 212 to a point where the compression member 208 is disposed adjacent to the tongs center portion 214 and where a distal end of the drive shaft 206 (i.e., the end furthest from the knob 244) would be located at about the position shown at reference numeral 228 of FIG. 4.

The compression member 208 is coupled to the drive shaft 206 by a ball joint 232 so that the compression member 208 moves in a generally linear, generally longitudinal direction in response to the movement of the drive shaft 206. In the illustrated embodiment, the ball joint 232 is comprised of a spherical portion 246 formed adjacent to the distal end of the drive shaft 206 and a cavity 248 defined by the compression member 208. The spherical portion 246 is configured to seat within the cavity 248 so that the spherical portion 246 can freely rotate within the cavity 248. While the spherical portion 246 and the cavity 248 are exposed to view in the illustrated embodiment, alternative embodiments include a cover (not shown) attached to the compression member 208 so that the spherical portion 246 and the cavity 248 are enclosed by the cover and are not exposed to view.

When the drive shaft 206 is moved from the second position to the first position, the compression member 208 slides from a position that is adjacent to the proximate end 210 of the tongs 204 (as illustrated in FIGS. 4 and 5) to a position adjacent to the center portion 214 of the tongs 204. Because the center portion 214 of the tongs 204 is a location where the first and second arms 218, 220 are separated by the relatively large first distance $d_1$ that is greater than the second distance $d_2$, this movement of the compression member 208 results in the outer wall 247 of each of the first and second channels 234, 236 acting to press inward or compress against the resilient first and second arms 218, 220 thereby overcoming their resiliency and exerting a closing force on them as well as on the first and second wedges 222, 224.

Prior to moving the drive shaft 206 from the second position to the first position, the arms and wedges are separated by a distance sufficient to allow for their insertion into the patient's mouth and for placement of the wedges 222, 224 between the adjacent teeth. On the other hand when the drive shaft 206 is rotated so that it is moved from the second position to the first position, the compression member 208 slides in a direction toward the distal end 212 of the tongs 204 and thereby imposes the closing force on the first and second arms 218, 220, thus allowing them and the wedges to move in the closing direction with sufficient force to separate the adjacent teeth. On the other hand when the drive shaft 206 is rotated in the opposite direction so that it is moved from the first position to the second position, the compression member 208 slides toward the proximate end 240 of the tongs 204, and thereby removes the closing force on the first and second arms 218, 220 and the first and second wedges 222, 224 so that they are no longer in contact with the adjacent teeth and can be easily removed from the patient's mouth. Thus the drive shaft 206 and the compression member 208 comprise means for exerting a closing force on the first and second arms 218, 220, for maintaining the closing force when a user is not grasping the tongs 204 or any other part of the separator apparatus 202, and for releasing the closing force.

As previously mentioned the first and second arms 218, 220 are constructed of a resilient material. They are formed to bias the first and second wedges 222, 224 away from each other when the compression force is removed thereby separating the first and second wedges 222, 224 by a distance sufficient to allow for their insertion into the patient's mouth and for placement of the first and second wedges between the adjacent teeth.

In the illustrated embodiment, the tongs 204, the housing 216, the first and second arms 218, 220, and the first and second wedges 222, 224 are constructed of metal and are monolithically formed. However in alternative embodiments, the wedges are removably attached to the arms. For example the wedges could be removably attached in the same manner as described above in connection with FIG. 6 or in connection with the other described embodiments.

According to an alternative embodiment of a separator apparatus, either the first arm 218 or the second arm 220 or both have a mechanical stop configured to prevent the compression member 208 from continuing to slide any further in the generally longitudinal direction toward the distal end 212 of the tongs 204. The mechanical stop could include any type of shoulder or protuberance that extends outwardly from one or both of the first and second arms 218, 220 so that it would act to block any further sliding movement of the compression member 208 and prevent any further closing of the first and second wedges 222, 224. In yet another embodiment, any further closing of the first and second wedges 222, 224 is prevented by a mechanical stop disposed on or adjacent to the external threads 226 of the drive shaft 206. This stop could include any type of shoulder or protuberance that would extend outwardly from the threads 226 for a distance sufficient to abut the housing 216 of the tongs 204 and prevent the drive shaft 206 from continuing to rotate and move any further in the generally longitudinal direction toward the distal end 212 of the tongs 204 when the drive shaft 206 reaches the first position. The foregoing embodiments having the mechanical stops are advantageous in that regardless of how much twisting force is exerted on the drive shaft 206, the separator apparatus 202 will only exert a maximum predetermined separation force on the adjacent teeth thus reducing the chances of causing harm to them.

In operation a user grasps the knob 244 with his/her fingers and rotates it and the drive shaft 206 so that the compression member 208 slides from the location adjacent to the center portion 214 of the tongs 204 to the location adjacent to the tongs proximate end 210. As the compression member 208 moves, it releases a compression force that had been exerted on the resilient first and second arms 218, 220 thereby allowing them and the first and second wedges 222, 224 to spread apart. Once the compression member 208 is positioned adjacent to the tongs proximate end 210 and the first and second wedges 222, 224 are spread apart, the user no longer needs to touch the knob 244 or any other portion of the drive shaft 206 or the tongs 204 in order to maintain the separation of the first and second wedges 222, 224.

Next the user inserts the first and second wedges 222, 224 and a portion of the first and second arms 218, 220 into the mouth of a patient, and then positions the first and second wedges 222, 224 adjacent to interdental surfaces of the adjacent teeth that are to be separated. The user then grasps the knob 244 and rotates it and the drive shaft 206 in the opposite direction, thereby sliding the compression member 208 back to its starting position that is adjacent to the tongs center portion 214. As the compression member 208 moves to this position, a compression or closing force is exerted on the first and second arms 218, 220 which overcomes their resiliency and causes them and the first and second wedges 122, 124 to move toward each other in a closing direction thereby exerting a closing force on the wedges that is sufficient to separate the adjacent teeth. After the dental work is completed on one or both of the adjacent, separated teeth, the user again rotates the knob 244 and drive shaft 206 so that the compression member 208 slides to the position that is adjacent to the tongs proximate end 210, thereby permitting the resiliency of the first and second arms 218, 220 to move them apart and to separate the first and second wedges 222, 224 so that they can be removed from contact with the adjacent teeth and can be easily removed from the patient's mouth.

In view of the above, it will be appreciated that certain embodiments of the invention overcome many of the long-standing problems in the art by providing a tooth separator apparatus that includes a pair of tongs having two arms constructed of a resilient material and having a wedge disposed at the end of each arm. An expander member is coupled to the two arms, and a drive shaft is coupled to the expander member. When a user moves or rotates the drive shaft, the expander member is moved into a position that causes the two arms and wedges to separate from one another by a distance sufficient to permit the wedges to be inserted in a patient's mouth and positioned adjacent to the interdental surfaces of two teeth that are to be separated. When the user rotates the drive shaft in the reverse direction, the expander member returns to its original position thereby releasing the separating force on the resilient arms and permitting them and the wedges to move in a closing direction with sufficient force to separate the adjacent teeth.

In an alternative embodiment, the resilient arms are biased in an open position. A drive shaft moves a compression member to overcome the resiliency of the arms and move them and the wedges in a closing direction for separating the teeth. The drive shaft can also move the compression member in the opposite direction to release the closing force on the arms and thereby permit their resiliency to allow them and the wedges to move to an open position.

While the description above refers to particular embodiments of the present invention, it will be understood that many modifications may be made without departing from the spirit thereof. The claims are intended to cover such modifications as would fall within the true scope and spirit of the present invention. The presently disclosed embodiments are therefore to be considered in all respects as illustrative and not restrictive, the scope of the invention being indicated by the claims rather than the foregoing description, and all changes which come within the meaning and range of equivalency of the claims are therefore intended to be embraced therein.

What is claimed is:

1. An apparatus for forcing apart adjacent teeth of a dental arch of a mouth, the apparatus comprising:
   tongs having a proximate end and a distal end, wherein the tongs are comprised of a first arm connected to a second arm at the proximate end,
      wherein the first arm has a first arm end and the second arm has a second arm end, wherein the first and second arm ends are disposed at the distal end of the tongs;
   a compression member in contact with the first and second arms; and
   a drive shaft coupled to the first and second arms by the compression member, wherein the drive shaft is configured to move the compression member, and wherein the drive shaft is further configured for movement between a first position and a second position,
      wherein the compression member is configured to exert a closing force on the first and second arms when the drive shaft is moved from the second position to the first position thereby moving the first and second arm ends toward each other with sufficient closing force to separate the adjacent teeth,
      wherein the compression member is further configured to exert the closing force by exerting an inward force on the first and second arms at a location on the first and second arms where the compression member is in contact with the first and second arms,
      wherein the compression member is further configured to remove the closing force from the first and second arms when the drive shaft is moved from the first position to the second position,
      wherein the first and second arms are constructed of a resilient material for biasing the first and second arm ends away from each other when the closing force is removed from the first and second arms, thereby separating the first and second arm ends by a distance sufficient to allow for insertion of the first and second arm ends into the mouth and for placement of the first and second arm ends between the adjacent teeth,
      wherein the first and second arms are shaped such that when the closing force is not exerted on the first and second arms, the first and second arms are separated by a first distance at a first location of the tongs and by a second distance at a second location of the tongs, wherein the first distance is greater than the second distance, and
      wherein the compression member is disposed adjacent to the first location of the tongs when the drive shaft is in the first position and disposed adjacent to the second location of the tongs when the drive shaft is in the second position.

2. The apparatus of claim 1 wherein the first arm end comprises a first wedge and the second arm end comprises a second wedge.

3. The apparatus of claim 2 wherein the tongs, the first and second arms, and the first and second wedges are integral.

4. The apparatus of claim 2 wherein the tongs, the first and second arms, and the first and second wedges are constructed of metal and are monolithically formed.

5. The apparatus of claim 2 wherein each of the first and second wedges has a shape configured to engage interdental surfaces of the adjacent teeth.

6. The apparatus of claim 2 wherein the first wedge is configured to slidably engage the first arm end and the second wedge is configured to slidably engage the second arm end, and wherein the first and second wedges are further configured to be removed from the first and second arm ends.

7. The apparatus of claim 1 further comprising:
   a first wedge and a second wedge; and
   means for removably attaching the first wedge to the first arm end and means for removably attaching the second wedge to the second arm end.

8. An apparatus for forcing apart adjacent teeth of a dental arch of a mouth, the apparatus comprising:
   tongs having a proximate end and a distal end, wherein the tongs are comprised of a first arm connected to a second arm at the proximate end,
      wherein the first arm has a first arm end and the second arm has a second arm end, wherein the first and second arm ends are disposed at the distal end of the tongs;
   a compression member in contact with the first and second arms; and
   a drive shaft coupled to the first and second arms by the compression member, wherein the drive shaft is configured to move the compression member, and wherein the drive shaft is further configured for movement between a first position and a second position,
      wherein the compression member is configured to exert a closing force on the first and second arms when the drive shaft is moved from the second position to the first position thereby moving the first and second arm ends toward each other with sufficient closing force to separate the adjacent teeth,
      wherein the compression member is further configured to exert the closing force by exerting an inward force on the first and second arms at a location on the first and second arms where the compression member is in contact with the first and second arms,
      wherein the compression member is further configured to remove the closing force from the first and second arms when the drive shaft is moved from the first position to the second position,
      wherein the first and second arms are constructed of a resilient material for biasing the first and second arm ends away from each other when the closing force is removed from the first and second arms, thereby separating the first and second arm ends by a distance sufficient to allow for insertion of the first and second arm ends into the mouth and for placement of the first and second arm ends between the adjacent teeth,
      wherein the tongs have a center portion disposed between the proximate end of the tongs and the distal end of the tongs,
      wherein the first and second arms are shaped such that when the closing force is not exerted on the first and second arms, the first and second arms are separated by a first distance at the center portion of the tongs and by a second distance at the proximate end of the tongs, wherein the first distance is greater than the second distance, and
      wherein the compression member is disposed adjacent to the proximate end of the tongs when the drive shaft is in the second position and disposed adjacent to the center portion of the tongs when the drive shaft is in the first position.

9. An apparatus for forcing apart adjacent teeth of a dental arch of a mouth, the apparatus comprising:

tongs having a proximate end and a distal end, wherein the tongs are comprised of a first arm connected to a second arm at the proximate end,
  wherein the first arm has a first arm end and the second arm has a second arm end, wherein the first and second arm ends are disposed at the distal end of the tongs;
a compression member disposed between the first and second arms and configured for slidable engagement with the first and second arms; and
a drive shaft coupled to the first and second arms by the compression member and configured for movement between a first position and a second position,
  wherein the compression member is coupled to the drive shaft by a ball joint,
  wherein the drive shaft and the compression member are further configured to exert a closing force on the first and second arms when the drive shaft is moved from the second position to the first position thereby moving the first and second arm ends toward each other with sufficient closing force to separate the adjacent teeth,
  wherein the drive shaft and the compression member are further configured remove the closing force from the first and second arms when the drive shaft is moved from the first position to the second position, and
  wherein the first and second arms are constructed of a resilient material for biasing the first and second arm ends away from each other when the closing force is removed from the first and second arms, thereby separating the first and second arm ends by a distance sufficient to allow for insertion of the first and second arm ends into the mouth and for placement of the first and second arm ends between the adjacent teeth.

10. An apparatus for forcing apart adjacent teeth of a dental arch of a mouth, the apparatus comprising:
tongs having a proximate end and a distal end, wherein the tongs are comprised of a first arm connected to a second arm at the proximate end,
  wherein the first arm has a first arm end and the second arm has a second arm end, wherein the first and second arm ends are disposed at the distal end of the tongs;
a compression member in contact with the first and second arms; and
a drive shaft coupled to the first and second arms by the compression member, wherein the drive shaft is configured to move the compression member, and wherein the drive shaft is further configured for movement between a first position and a second position,
  wherein the compression member is configured to exert a closing force on the first and second arms when the drive shaft is moved from the second position to the first position thereby moving the first and second arm ends toward each other with sufficient closing force to separate the adjacent teeth,
  wherein the compression member is further configured to exert the closing force by exerting an inward force on the first and second arms at a location on the first and second arms where the compression member is in contact with the first and second arms,
  wherein the compression member is further configured to remove the closing force from the first and second arms when the drive shaft is moved from the first position to the second position,
  wherein the first and second arms are constructed of a resilient material for biasing the first and second arm ends away from each other when the closing force is removed from the first and second arms, thereby separating the first and second arm ends by a distance sufficient to allow for insertion of the first and second arm ends into the mouth and for placement of the first and second arm ends between the adjacent teeth, and
  wherein the compression member is comprised of a rigid piece configured to slidably receive each of the first and second arms of the tongs.

11. The apparatus of claim 10 wherein the compression member is configured to slide in a generally longitudinal direction toward the distal end of the tongs as the drive shaft moves from the second position to the first position,
  wherein one of the first arm and the second arm has a mechanical stop configured to prevent the compression member from continuing to slide any further in the generally longitudinal direction toward the distal end of the tongs.

12. An apparatus for forcing apart adjacent teeth of a dental arch of a mouth, the apparatus comprising:
tongs having a proximate end and a distal end, wherein the tongs are comprised of a first arm connected to a second arm at the proximate end,
  wherein the first arm has a first arm end and the second arm has a second arm end, wherein the first and second arm ends are disposed at the distal end of the tongs;
a compression member in contact with the first and second arms; and
a drive shaft coupled to the first and second arms by the compression member, wherein the drive shaft is configured to move the compression member, and wherein the drive shaft is further configured for movement between a first position and a second position,
  wherein the compression member is configured to exert a closing force on the first and second arms when the drive shaft is moved from the second position to the first position thereby moving the first and second arm ends toward each other with sufficient closing force to separate the adjacent teeth,
  wherein the compression member is further configured to exert the closing force by exerting an inward force on the first and second arms at a location on the first and second arms where the compression member is in contact with the first and second arms,
  wherein the compression member is further configured to remove the closing force from the first and second arms when the drive shaft is moved from the first position to the second position,
  wherein the first and second arms are constructed of a resilient material for biasing the first and second arm ends away from each other when the closing force is removed from the first and second arms, thereby separating the first and second arm ends by a distance sufficient to allow for insertion of the first and second arm ends into the mouth and for placement of the first and second arm ends between the adjacent teeth, and
  wherein the compression member is comprised of a rigid piece that defines a first channel configured to slidably mate with the first arm of the tongs and a second channel configured to slidably mate with the second arm of the tongs.

13. An apparatus for forcing apart adjacent teeth of a dental arch of a mouth, the apparatus comprising:
tongs having a proximate end and a distal end, wherein the tongs are comprised of a first arm connected to a second arm at the proximate end, wherein the first arm has a first arm end and the second arm has a second arm end, wherein the first and second arm ends are disposed at the distal end of the tongs;

a compression member disposed between the first and second arms and configured for slidable engagement with the first and second arms; and a drive shaft coupled to the first and second arms by the compression member and configured for movement between a first position and a second position, wherein the drive shaft and the compression member are further configured to exert a closing force on the first and second arms when the drive shaft is moved from the second position to the first position thereby moving the first and second arm ends toward each other with sufficient closing force to separate the adjacent teeth, wherein the drive shaft and the compression member are further configured remove the closing force from the first and second arms when the drive shaft is moved from the first position to the second position, wherein the first and second arms are constructed of a resilient material for biasing the first and second arm ends away from each other when the closing force is removed from the first and second arms, thereby separating the first and second arm ends by a distance sufficient to allow for insertion of the first and second arm ends into the mouth and for placement of the first and second arm ends between the adjacent teeth, wherein the tongs include a housing disposed at the proximate end of the tongs, wherein the housing defines a longitudinally-oriented port having internal threads, wherein the drive shaft includes external axial threads configured to engage the internal threads of the housing, and wherein the compression member is coupled to the drive shaft by a ball joint.

14. The apparatus of claim 13 wherein the drive shaft is configured to rotate so that the drive shaft moves in a generally longitudinal direction toward the distal end of the tongs as the drive shaft moves from the second position to the first position, wherein the drive shaft has a mechanical stop disposed adjacent to the external threads and configured to abut the housing of the tongs and prevent the drive shaft from continuing to move any further in the generally longitudinal direction toward the distal end of the tongs when the drive shaft reaches the first position.

15. An apparatus for forcing apart adjacent teeth of a dental arch of a mouth, the apparatus comprising:

tongs having a proximate end, a distal end and a housing disposed at the proximate end, wherein the tongs are comprised of a first arm connected to a second arm at the proximate end, and wherein the housing defines a longitudinally-oriented port having internal threads;

a first wedge connected to the first arm and a second wedge connected to the second arm, wherein the first and second wedges are disposed at the distal end of the tongs;

a drive shaft having external axial threads configured to rotatably engage the internal threads of the housing of the tongs, wherein the drive shaft is configured for a generally linear movement between a first position and a second position in response to a rotation of the drive shaft; and a compression member coupled to the drive shaft by a ball joint so that the compression member moves in a generally linear direction in response to the generally linear movement of the drive shaft, wherein the compression member is comprised of a rigid piece defining a first channel configured to slidably mate with the first arm of the tongs and a second channel configured to slidably mate with the second arm of the tongs, wherein the drive shaft and the compression member are further configured to exert a closing force on the first and second arms when the drive shaft is moved from the second position to the first position thereby moving the the first and second wedges toward each other with sufficient closing force to separate the adjacent teeth, wherein the drive shaft and compression member are further configured to remove the closing force from the first and second arms when the drive shaft is moved from the first position to the second position, wherein the first and second arms are formed to bias the first and second wedges away from each other when the closing force is removed from the first and second arms, thereby separating the first and second wedges by a distance sufficient to allow for insertion of the first and second wedges into the mouth and for placement of the first and second wedges between the adjacent teeth, wherein the first and second arms are shaped such that when the closing force is not exerted on the first and second arms, the first and second arms are separated by a first distance at a first location of the tongs and by a second distance at a second location of the tongs, wherein the first distance is greater than the second distance, and wherein the compression member is disposed adjacent to the first location of the tongs when the drive shaft is in the first position and disposed adjacent to the second location of the tongs when the drive shaft is in the second position.

16. The apparatus of claim 15 wherein the tongs, the housing, the first and second arms, and the first and second wedges are constructed of metal and are monolithically formed.

* * * * *